United States Patent [19]

Shimizu et al.

[11] Patent Number: 4,728,509
[45] Date of Patent: Mar. 1, 1988

[54] AQUEOUS LIQUID PREPARATION

[75] Inventors: Hisayoshi Shimizu, Ibaraki; Mitsuaki Oshima, Suita; Hideo Terayama, Itami, all of Japan

[73] Assignees: Takeda Chemical Industries, Ltd.; Senju Pharmaceutical Co., Ltd., both of Osaka, Japan

[21] Appl. No.: 893,161

[22] Filed: Aug. 5, 1986

[30] Foreign Application Priority Data

Aug. 19, 1985 [JP]  Japan .................................. 60-182383

[51] Int. Cl.$^4$ ...................... A61K 31/44; A61K 31/78
[52] U.S. Cl. ......................................... 424/81; 514/291
[58] Field of Search ........................... 424/81; 514/291

[56] References Cited

U.S. PATENT DOCUMENTS

| 3,927,205 | 12/1975 | Ohno et al. | 424/80 |
| 4,143,042 | 3/1979 | Nohara et al. | 546/92 |
| 4,344,968 | 8/1982 | Aoda et al. | 424/81 |
| 4,539,326 | 9/1985 | Nohara et al. | 514/291 |

FOREIGN PATENT DOCUMENTS

| 0082921 | 8/1982 | European Pat. Off. |
| 0094157 | 4/1983 | European Pat. Off. |
| 0119737 | 2/1984 | European Pat. Off. |
| 0105635 | 4/1984 | European Pat. Off. |
| 191568 | 8/1986 | European Pat. Off. | 514/291 |
| 7498 | 2/1951 | German Democratic Rep. |
| 54-115398 | 7/1979 | Japan | 514/291 |

OTHER PUBLICATIONS

Patent Abstracts of Japan, Unexamined Applications, Section C, Vol. 8, No. 222, Oct. 9, 1984, p. 85 C 246, Kokai No. 59-106 424 Kiyourin Seikaku K.K.

Primary Examiner—Douglas W. Robinson
Attorney, Agent, or Firm—Wegner & Bretschneider

[57] ABSTRACT

In the aqueous liquid preparation of this invention, which comprises a compound of the formula;

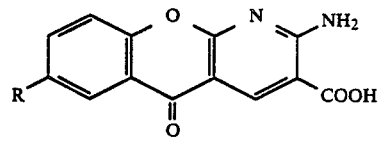

wherein R is an alkyl having 1-6 carbon atoms, and at least one species of the solubilizers selected from the group consisting of polyvinylpyrrolidone, cyclodextrin and caffeine, the solubility of the compound in water can be heightened and the aqueous liquid prepared thereby can afford a desired stability and mitigate eye-irritation or nose-irritation.

12 Claims, No Drawings

AQUEOUS LIQUID PREPARATION

This invention relates to an aqueous liquid preparation, which comprises a compound (A) of the formula;

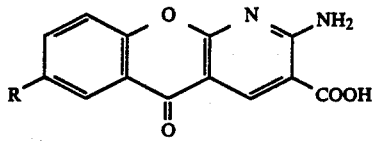

wherein R is an alkyl having 1-6 carbon atoms, and at least one species of the solubilizers selected from the group consisting of polyvinylpyrrolidone, cyclodextrin and caffeine.

The above-mentioned compound (A) has both an inhibitory action against the formation of SRS-A (slow reacting substance of anaphylaxis) and an antagonistic action on SRS-A, is a drug for controlling histamine liberation due to IgE-originating allergy, and has been known to have a strong anti-allergic and an anti-inflammatory action (U.S. Pat. No. 4,143,042). Because of the strong anti-allergic action and anti-inflammatory action, the compound (A) is useful as a nasal drop, an eye drop or a drug for oral application.

In local administration of this drug as an aqueous liquid preparation such as in nasal drops or eye drops, the concentration required is generally 1-10 mg/ml.

However, the solubility of the compound (A) in water is very low. For example, the solubility of the compound (A) whose R is isopropyl [hereinafter referred to a compound (a)] is only about 0.01 mg/ml at 25° C. Therefore, preparation of compound (a) into a liquid preparation was extremely difficult.

To solve the above-mentioned problem, the present inventors conducted an intensive study on liquid preparations containing the compound (A) and found that polyvinylpyrrolidone, cyclodextrin or caffeine serve to remarkably enhance the solubility of the compound (A).

This invention relates to an aqueous liquid preparation which comprises the compound (A) and at least one species of the solubilizers selected from the group consisting of polyvinylpyrrolidone, cyclodextrin and caffeine.

Aqueous liquid preparations obtainable by the present invention are exemplified by nasal drops, eye drops, liniments, ointments, inhalants, internals and injections.

Solubilizers to be incorporated for enhancing the solubility of the compound (A) in water are exemplified by polyvinylpyrrolidone, cyclodextrin and caffeine. Among these, polyvinylpyrrolidone has an especially remarkable effect, stabilizing the resultant aqueous liquid solution with great effectiveness.

An aqueous liquid preparation is obtained by dissolving the compound (A) and at least one of the aboveexemplified solubilizers. The compound (A) content of the aqueous liquid preparation is in the range of from 0.05 to 2 (w/v)%, preferably 0.1-1 (w/v)%.

As the polyvinylpyrrolidone employable in the present invention, there may be mentioned those having a average molecular weight of about 25,000–about 120,000, preferably about 40,000.

The amount of polyvinylpyrrolidone to be added is usually 0.2-20 (W/V)%, preferably 0.5-15 (W/V)%, and, especially for preparing eye drops, 1-10 (W/V)% is preferable.

The cyclodextrin employable in the present invention may be any of α-form, β-form and γ-form.

The amount of cyclodextrin to be added is usually 0.2-5 (W/V)%, preferably 0.5-2 (W/V)%.

The amount of caffeine to be added is usually 0.1∼2 (W/V)%, preferably 0.2∼1 (W/V)%.

The aqueous liquid preparation of this invention may be incorporated with a usually employable amount of additives conventionally usable for aqueous liquid preparations, for example, a buffering agent for pH adjustment (phosphate buffer, borate buffer, citrate buffer, tartrate buffer, acetate buffer, etc.), an isotonizing agent (sorbitol, glycerin, polyethylene glycol, propylene glycol, glucose, sodium chloride, etc.), a preservative (p-hydroxybenzoic acid esters, benzyl alcohol, p-chlorom-xylenol, chloro-cresol, phenethyl alcohol, sorbic acid or its salt, thimerosal, chloro-butanol, etc.), a chelating agent (sodium edetate, sodium citrate, condensed sodium phosphate, etc.) a thickening agent (carboxymethylcellulose sodium, hydroxyethylcellulose, hydroxypropylcellulose, methylcellulose, polyvinyl alcohol, sodium polyacrylate), etc.

The aqueous liquid preparations may be employed in the region between pH 5 and pH 8, considering the stability of the compound (A).

Among the liquid preparations of this invention, further explanation is made regarding nasal drop preparations and eye drop preparations. These preparations are required to be in the state of complete solution even when placed in a cold chamber. However, the compound (A) has a very low solubility in water, for example the compound (a), which is the compound (A) wherein R is isopropyl, dissolves only to an extent of 0.3 mg/ml at pH 7.5 in a cold chamber (5° C.).

For local administration at the site of e.g. nose and eyes, especially sensitive to stimulation, the neutral to alkaline region (pH 7.2–7.8) is preferable. Within the region, the solubility of the compound (a) is about 1.1 mg/ml, but the aqueous liquid preparation of this invention is capable of dissolving the compound (a) to an extent of 3 mg/ml or more. While the compound (A) is decomposed and unstable in its aqueous solution of a pH preferable for nasal drops or eye drops, for example an aqueous solution of pH 7.5, polyvinylpyrrolidone has especially excellent action in stabilizing it.

In the nasal drops and eye drops of this invention, use of boric acid as the buffering agent gives a less irritating liquid preparation, as compared with the case of using other buffering agents such as phosphoric acid. The amount of boric acid to be added ranges from 0.2 to 4 (W/V)%, preferably 0.5-3 (W/V)%.

The method for preparing aqueous liquid preparations varies with the kinds of liquid preparations, and each kind can be produced by any of the per se known methods. For example, a nasal drop preparation or an eye drop preparation can be produced by heating purified water, dissolving a preservative therein, then adding thereto a solubilizer, followed by, if necessary, adding, for example, a buffering agent, an isotonizing agent, a chelating agent and a thickening agent and so on, and then compound (A) to make a complete solution.

In the aqeous liquid preparation of this invention, the solubility of the compound (A) in water is heightened by providing at least one species of the solubilizers selected from the group consisting of polyvinylpyrrolidone, cyclodextrin and caffeine; the concentration of the compound (A) can be increased so that the therapeutic effect is obtained, with provision of desired stability. Therefore, the excellent anti-allergic action and anti-inflammatory action of the compound (A) can be provided.

By further incorporating boric acid into the aqueous liquid preparation in addition to the compound (A) and the solubilizer, eye-irritation can be mitigated to a further extent.

EXAMPLES

The following Experimental Examples and Examples illustrate the invention in more detail.

EXPERIMENTAL EXAMPLE 1

Solubility Test:

Solubility tests of the compound (a) (2-amino-7-isopropyl-5-oxo-5H-[1]-benzopyrano[2,3-b]pyridine-3-carboxylic acid) employing the solubilizers of this invention and, for comparison, employing various conventional solubilizers were performed.

As the solubilizers of this invention were employed polyvinylpyrrolidone (average molecular weight 40,000), $\beta$-cyclodextrin and caffeine, and as the conventional solubilizers were employed nonionic surfactants (polyoxyethylene hydrogenated castor oil, polyoxyethylene fatty acid ester, sucrose fatty acid ester, etc.), sodium benzoate, sodium salicylate, urea, sodium L-glutamate, nicotininc acid amide and isoniazid.

Among these, Tween 80, sodium benzoate, sodium salicylate, urea, and sodium L-glutamate were less effective for improving the solubility, while some improvement was observed by employing nicotinic acid and isoniazid. In contrast thereto, polyvinylpyrrolidone (average molecular weight 40,000), $\beta$-cyclodextrin and caffeine showed excellent effect in improvement of the solubility.

The solubility was measured by the following manner:

An excess amount of the compound (a) was added to a given volume of a phosphate buffer, the mixture was sufficiently stirred, then the pH was adjusted to a given level, the mixture was allowed to stand at room temperature (25° C.) for 48 hours, the resultant was subjected to filtration with 0.45$\mu$ membrane filter, followed by measuring the concentration of the compound (a) in the filtrate by means of high performance liquid chromatography. The results were shown in Table B 1.

TABLE 1

| Solubilizers | Additive amount (mg/ml) | The Solubility of Compound (a) [Note 1] | | | |
|---|---|---|---|---|---|
| | | pH 6.0 | pH 6.5 | pH 7.0 | pH 7.5 |
| Control | — | 0.02 | 0.08 | 0.33 | 1.05 |
| Tween 80 [Note 2] | 10 | 0.08 | 0.47 | — | 1.18 |
| Sodium benzoate | 20 | 0.04 | 0.29 | 0.42 | 1.06 |
| Nicotinic acid amide | 10 | — | 0.82 | 1.21 | 1.53 |
| Isoniazid | 10 | — | 0.85 | 1.33 | 1.56 |
| Caffeine | 5 | 0.66 | 1.50 | 3.72 | 7.44 |
| Caffeine | 10 | 1.65 | 2.67 | 7.05 | 9.21 |
| $\beta$-Cyclodextrin | 10 | 0.72 | 1.40 | 2.30 | 4.39 |
| Polyvinylpyrrolidone (Average molecular weight 40000) | 10 | 0.12 | 0.42 | 1.06 | 3.15 |
| Polyvinylpyrrolidone (Average molecular weight 40000) | 50 | 0.32 | 1.23 | 3.23 | 10.36 |
| Polyvinylpyrrolidone (Average molecular weight 40000) | 100 | 1.59 | 4.63 | 10.04 | 18.46 |

TABLE 1-continued

| Solubilizers | Additive amount (mg/ml) | The Solubility of Compound (a) [Note 1] | | | |
|---|---|---|---|---|---|
| | | pH 6.0 | pH 6.5 | pH 7.0 | pH 7.5 |

[Note 1] Unit of solubility of the compound (a) is mg/ml.
[Note 2] Polyoxyethylene sorbitan mono-oleate

EXPERIMENTAL EXAMPLE 2

Stability Test:

The stability of the compound (a) was tested by the following manner.

At first, the stability of the compound (a) without any adjuvant was tested for comparison.

Two samples were prepared by dissolving 100 mg and 250 mg each portion of the compound (a) in phosphate buffer. To each of the solutions was added a solution of sodium hydroxide to adjust the pH to 7.5±0.1, followed by addition of purified water to make the whole volume 100 ml, provided that the solution of 2.5 mg/ml was prepared at 40° C. Each solution was filled in a glass bottle, which was stored at 60° C. for evaluation of the stability.

The results were shown in Table 2 as remaining ratio (%).

TABLE 2

| Content of Compound (a) | 1.0 mg/ml | 2.5 mg/ml |
|---|---|---|
| 60° C. after one week | 99.2% | 92.1% |
| 60° C. after two weeks | 97.2% | 80.5% |
| 60° C. after four weeks | 85.4% | 66.8% |

Next, the effect of improving the stability of the compound (a), when a solubilizer of this invention was added to the solution containing the compound (a), was examined.

Samples having the respective concentrations as shown in Table 3 were prepared. To each sample was added a given amount of a solubilizer as specified in the table, followed by working up in a similar manner to the above (pH 7.5±0.1) for evaluation of the stability.

The results were shown in Table 3 as remaining ratio (%).

TABLE 3

| Content of Compound (a) | 1.0 mg/ml | 2.5 mg/ml | 5.0 mg/ml | 10.0 mg/ml |
|---|---|---|---|---|
| Amount of Solubilizer added | | | | |
| PVP* (average molecular weight 40,000) | 20 mg/ml | 50 mg/ml | 10 mg/ml | 50 mg/ml |
| Caffeine | — | — | 10 mg/ml | — |
| $\beta$-CD** | — | — | — | 10 mg/ml |
| 60° C. after 1 week | 99.5% | 98.9% | 98.9% | 98.7% |
| 60° C. after 2 weeks | 99.2% | 99.5% | 99.5% | 100.1% |
| 60° C. after 4 weeks | 98.4% | 99.1% | 98.1% | 98.3% |
| 60° C. after 8 weeks | 98.1% | 97.0% | 98.2% | 97.3% |

*PVP = polyvinylpyrrolidone
**$\beta$-CD = $\beta$-cyclodextrin

EXPERIMENTAL EXAMPLE 3

Eye Irritation Test:

For conducting eye irritation test, the criteria were set as follows:

Eye drop preparations prescribed as the following 1, 2, 3 and 4 were instilled into eyes of 10 healthy men, and eye-irritation degrees were compared among them.

Prescription 1

In 100 ml of 0.04M phosphate buffer of pH 7.4 was dissolved 620 mg of sodium chloride, and the solution was subjected to filtration and sterilization.

Prescription 2

In 100 ml of 0.04M phosphate buffer of pH 6.5 was dissolved 660 mg of sodium chloride, and the solution was subjected to filtration and sterilization.

Prescription 3

In 100 ml of 0.04M phosphate buffer of pH 5.5 was dissolved 680 mg of sodium chloride, and the solution was subjected to filtration and sterilization.

Prescription 4

In 100 ml of 0.04M phosphate buffer of pH 4.5 was dissolved 680 mg of sodium chloride, and the solution was subjected to filtration and sterilization.

The results are shown in Table 4.

TABLE 4

| Subject | Prescription 1 | Prescription 2 | Prescription 3 | Prescription 4 |
|---|---|---|---|---|
| 1 | — | +1 | +2 | +4 |
| 2 | — | +1 | +3 | +4 |
| 3 | — | +1 | +2 | +3 |
| 4 | +1 | +2 | +3 | +4 |
| 5 | — | +1 | +2 | +2 |
| 6 | +1 | +2 | +3 | +4 |
| 7 | — | +1 | +3 | +3 |
| 8 | — | +1 | +2 | +4 |
| 9 | — | +1 | +2 | +4 |
| 10 | +1 | +1 | +3 | +4 |

The criteria of irritation were set as follows:

| — | No irritable and unpleasant feeling (instilled with Prescription 1) | point 0 |
|---|---|---|
| +1 | A little irritant (instilled with Prescription 2) | point 1 |
| +2 ~ +3 | Irritant (instilled with Prescription 3) | point 2-3 |
| +4 | Strong irritation (instilled with Prescription 4) | point 4 |

Based on these criteria, the following 1, 2, 3 and control eye-drop preparations were instilled into eyes of 10 healthy men, and the degrees of eye-irritation were compared among them.

Eye Drop Preparation Prescription 1

Prescription

Compound (a): 2.5 g
Boric acid: 16 g
Borax: 7 g
Polyvinylpyrrolidone (average molecular weight 40,000): 20 g
Methyl parahydroxybenzoate: 0.26 g
Propyl parahydroxybenzoate: 0.14 g
Sterile purified water, q.s.: 1.0 l (in total)

Preparation

In 800 ml of heated sterile purified water were dissolved methyl parahydroxybenzoate and propyl parahydroxybenzoate. To the solution were added boric acid, borax, polyvinylpyrrolidone (average molecular weight 40,000) and the compound (a) sequently to make a solution. To this solution was added, after cooling, sterile purified water to make the whole volume 1.0 l. The solution was subjected to filtration with 0.22μ membrane filter and was sterilized, followed by filling into containers to afford an eye drop preparation showing excellent stability.

Eye Drop Preparation Prescription 2

Except using 10 g of β-cyclodextrin instead of 20 g of polyvinylpyrrolidone (average molecular weight 40,000), the same procedure as the Eye Drop Preparation Prescription 1 was taken to give an eye drop preparation.

Eye Drop Preparation Prescription 3

In 800 ml of heated sterile purified water were dissolved 0.26 g of methyl parahydroxybenzoate and 0.14 g of propyl parahydroxybenzoate. In the solution were dissolved 2.5 g of the compound (a), 4.0 g of dibasic sodium phosphate, 8.5 g of sodium chloride and 20 g of polyvinylpyrrolidone (average molecular weight 40,000). After cooling, the pH of the solution was adjusted to 7.5 with the addition of 0.48 g of sodium hydroxide, followed by addition of sterile purified water to make the whole volume 1.0 l., which was subjected to filtration with 0.22μ membrane filter and was sterilized. The solution obtained was filled into containers to afford an eye drop preparation showing excellent stability.

Control Prescription

An eye drop preparation was prepared in a manner similar to the above Prescription 3, except for omitting the incorporation of polyvinylpyrrolidone (average molecular weight 40,000).

This preparation was used promptly after prescription, because, when this preparation is allowed to stand at room temperature, it produces precipitates of hardly soluble compound (a).

The results were shown in Table 5.

TABLE 5

| Subject | Eye Drop Preparation Prescription | | | Control Prescription |
|---|---|---|---|---|
|  | 1 | 2 | 3 |  |
| 1 | 2 | 0 | 2 | 3 |
| 2 | 0 | 1 | 1 | 1 |
| 3 | 0 | 0 | 1 | 2 |
| 4 | 0 | 0 | 0 | 2 |
| 5 | 1 | 1 | 2 | 2 |
| 6 | 1 | 2 | 1 | 4 |
| 7 | 0 | 0 | 0 | 0 |
| 8 | 0 | 2 | 3 | 3 |
| 9 | 0 | 1 | 1 | 3 |
| 10 | 1 | 1 | 1 | 2 |
| Average | 0.5 | 0.8 | 1.2 | 2.2 |

From the above table, as compared with the control prescription, each eye drop preparation prescribed as above 1, 2 and 3 was found to be little irritating, especially the prescriptions 1 and 2 incorporated with boric acid performing a remarkable effect of decreasing eye irritation.

In the above-mentioned prescriptions 1 and 2 as well as in the working examples 3 and 4 to be described hereafter, borax is employed together with boric acid. In these exemplified preparations, boric acid acts as an agent for mitigating eye irritation as well as a buffering agent for adjusting the pH in concert with borax.

EXAMPLE 1

(Nasal Drop)

Prescription

Compound (a): 10 g
Dibasic sodium phosphate: 10 g
Monobasic sodium phosphate: 1.7 g Polyvinylpyrrolidone (average molecular weight 25,000): 50 g
β-cyclodextrin: 10 g
Conc. glycerin: 0.3 g
Sodium hydroxide: 1.7 g
Methyl parahydroxybenzoate: 2.0 g
Propyl parahydroxybenzoate: 0.5 g
Benzyl alcohol: 3.0 g
Purified water, q.s.: 1.0 l (in total)

Preparation

In 800 ml of heated purified water were dissolved methyl parahydroxybenzoate and propyl parahydroxybenzoate, followed by addition of dibasic sodium phosphate, monobasic sodium phosphate, polyvinylpyrrolidone (average molecular weight 25,000), β-cyclodextrin and concentrated glycerin in sequence to make a solution. In the solution was then dissolved the compound (a). After cooling, benzyl alcohol (a preservative) was dissolved in the solution, whose pH was adjusted to 7.5 with the addition of sodium hydroxide, followed by addition of purified water to make the whole volume 1.0 l. The solution was subjected to filtration with 0.45μ membrane filter, followed by filling into containers to afford a nasal drop liquid preparation.

EXAMPLE 2

(Nasal Drop)

Prescription

Compound (a): 2.5 g
Dibasic sodium phosphate: 10 g
Monobasic sodium phosphate: 3 g
Polyvinylpyrrolidone (average molecular weight 40,000): 10 g
Caffeine: 10 g
Sodium chloride: 0.3 g
Sodium hydroxide: 1.0 g
Propyl parahydroxybenzoate: 0.35 g
Butyl parahydroxybenzoate: 0.1 g
Purified water, q.s.: 10 l (in total)

Preparation

In 800 ml of heated purified water were dissolved propyl parahydroxybenzoate and butyl parahydroxybenzoate. To the solution were added in sequence dibasic sodium phosphate, monobasic sodium phosphate, polyvinylpyrrolidone (average molecular weight 40,000), caffeine and sodium chloride to make a solution, in which was dissolved the compound (a). After cooling, pH of the solution was adjusted to 6.5 by the addition of sodium hydroxide, followed by addition of purified water to make the whole volume 1.0 l. The solution was subjected to filtration with 0.45μ membrane filter, and the filtrate was filled into containers to afford a nasal drop liquid preparation.

EXAMPLE 3

(Nasal Drop)

Prescription

Compound (a): 2.5 g
Monobasic sodium phosphate: 1.7 g
Dibasic sodium phosphate: 10 g
Sodium hydroxide: 0.6 g
Polyvinylpyrrolidone (average molecular weight 25,000): 50 g
Conc. glycerin: 10 g
Butyl parahydroxybenzoate: 0.1 g
Propyl parahydroxybenzoate: 0.35 g
Benzyl alcohol: 3 g
Purified water, g.s.: 1.0 l (in total)

Preparation

In 800 ml of heated purified water were dissolved butyl parahydroxybenzoate and propyl parahydroxybenzoate, followed by addition of monobasic sodium phosphate, dibasic sodium phosphate, polyvinylpyrrolidone (average molecular weight 25,000) and concentrated glycerin in sequence to make a solution. In the solution was then dissolved the compound (a). After cooling, benzyl alcohol was dissolved in the solution, whose pH was adjusted to 7.5 with the addition of sodium hydroxide, followed by addition of purified water to make the whole volume 1.0 l. The solution was subjected to filtration with 0.45μ membrane filter, followed by filling into containers to afford a nasal drop liquid preparation.

EXAMPLE 4

(Nasal Drop)

Prescription

Compound (a): 2.5 g
Monobasic sodium phosphate: 1.7 g
Dibasic sodium phosphate: 10 g
Sodium hydroxide: 0.6 g
Caffeine: 10 g
Conc. glycerin: 5 g
Butyl parahydroxybenzoate: 0.1 g
Propyl parahydroxybenzoate: 0.35 g
Purified water, g.s.: 1.0 l (in total)

Preparation

In 800 ml of heated purified water were dissolved butyl parahydroxybenzoate and propyl parahydroxybenzoate, followed by addition of monobasic sodium phosphate, dibasic sodium phosphate, caffeine and concentrated glycerin in sequence to make a solution. In the solution was then dissolved the compound (a). After cooling, the pH of the solution was adjusted to 7.5 with the addition of sodium hydroxide, followed by addition of purified water to make the whole volume 1.0 l. The solution was subjected to filtration with 0.45μ membrane filter, followed by filling into containers to afford a nasal drop liquid preparation.

EXAMPLE 5

(Eye Drop)

Prescription

Compound (a): 5 g
Boric acid: 16 g
Borax: 10 g
Polyvinylpyrrolidone (average molecular weight 40,000): 20 g
Caffeine: 2 g
Polyethylene glycol (average molecular weight 4,000): 5 g
Methyl parahydroxybenzoate: 0.26 g
Propyl parahydroxybenzoate: 0.14 g
Sterile purified water, q.s.: 1.0 l (in total)

Preparation

In 800 ml of heated sterile purified water were dissolved methyl parahydroxybenzoate and propyl parahydroxybenzoate. To the solution were added in sequence boric acid, borax, polyvinylpyrrolidone (average molecular weight 40,000), caffeine, polyethylene glycol and the compound (a) to make a solution, to which, after cooling, was added sterile purified water to make the whole volume 1.0 l. The solution was subjected to filtration with 0.22μ membrane filter and was sterilized. The filtrate was filled into containers to afford an eye drop liquid preparation (pH about 7.5).

EXAMPLE 6

(Eye drop)

Prescription
Compound (a): 1 g
Boric acid: 16 g
Borax: 7 g
β-cyclodextrin: 10 g
Thimerosal: 0.01 g
Sterile purified water, q.s.: 1.0 l (in total)
Preparation To 800 ml of heated sterile purified water were added in sequence boric acid, borax, β-cyclodextrin and the compound (a) to make a solution. In the solution, after cooling, was dissolved thimerosal, followed by addition of sterile purified water to make the whole volume 1.0 l. The solution was subjected to filtration with 0.22μ membrane filter and was sterilized. The filtrate was filled into containers to afford an eye drop liquid preparation (pH about 7.5).

EXAMPLE 7

(Inhalant)

Compound (a): 5 g
Caffeine: 5 g
Polyvinylpyrrolidone (average molecular weight 25,000): 20 g
Polyethylene glycol (average molecular weight 1,000): 2 g
Dibasic sodium phosphate: 6 g
Citric acid: 0.8 g
Methyl parahydroxybenzoate: 2.0 g
Propyl parahydroxybenzoate: 0.5 g
Purified water, q.s.: 1000 ml (in total)
Preparation In 800 ml of heated purified water were dissolved methyl parahydroxybenzoate and propyl parahydroxybenzoate. To the solution were added dibasic sodium phosphate, citric acid, polyvinylpyrrolidone (average molecular weight 25,000), polyethylene glycol (average molecular weight 1,000) and the compound (a) to make a solution, followed by addition of purified water to make the whole volume 100 ml. The solution was then subjected to filtration with 0.22μ membrane filter. The filtrate was filled in a container to afford an inhalant (pH about 7.0).

EXAMPLE 8

(Liniment)

Compound (a): 10 g
Polyvinylpyrrolidone (average molecular weight 40,000): 50 g
β-cyclodextrin: 10 g
Carboxyvinyl polymer (average molecular weight 2-3 million): 0.5 g
Boric acid: 16 g
Borax: 10 g
Sodium hydroxide: 0.2 g
Thimerosal: 0.02 g
Purified water, q.s.: 1000 g (in total)
Preparation In 200 g of purified water were dissolved boric acid, borax, sodium hydroxide and thimerosal. [Solution (1)] In 600 g of purified water were dispersed homogeneously polyvinylpyrrolidone (average molecular weight 40,000), β-cyclodextrin and carboxyvinyl polymer (average molecular weight 2-3 million). [Solution (2)] To solution (2) was gradually added Solution (1) to give a transparent gel.

To this gel was gradually added the compound (a) while stirring to afford a gel liniment.

What we claim is:

1. An aqueous liquid composition, which comprises a therapeutically effective amount of a compound of the formula;

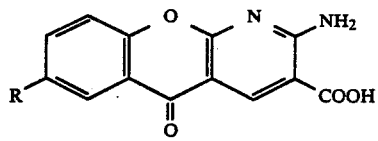

wherein R is an alkyl having 1-6 carbon atoms, and at least one solubilizer selected from the group consisting of polyvinylpyrrolidone in an amount of about 0.2-20% (W/V), cyclodextrin in an amount of about 0.2-5% (W/V), and caffeine in an amount of about 0.1-2% (W/V).

2. An aqueous liquid composition as claimed in claim 1, wherein the preparation is for a nasal drop.

3. An aqueous liquid composition as claimed in claim 1, wherein the preparation is for an eye drop.

4. An aqueous liquid composition as claimed in claim 1, wherein the preparation is further incorporated with boric acid.

5. An aqueous liquid composition as claimed in claim 1, wherein the solubilizer is polyvinylpyrrolidone.

6. An aqueous liquid composition as claimed in claim 1, wherein the solubilizer is cyclodextrin.

7. An aqueous liquid composition as claimed in claim 1, wherein the solubilizer is caffeine.

8. An aqueous liquid composition as claimed in claim 1, wherein the compound is 2-amino-7-isopropyl-5-oxo-5H-[1]benzopyrano[2,3-b]pyridine-3-carboxylic acid.

9. An aqueous liquid composition as claimed in claim 5 wherein the polyvinylpyrrolidone is present in an amount of about 0.5-15% (W/V).

10. An aqueous liquid composition as claimed in claim 5 wherein the polyvinylpyrrolidone is present in an amount of about 10-10% (W/V).

11. An aqueous liquid composition as claimed in claim 6 wherein the cyclodextrin is present in an amount of about 0.5-2% (W/V).

12. An aqueous liquid composition as claimed in claim 7 wherein the caffeine is present in an amount of about 0.2-1.0% (W/V).

* * * * *

UNITED STATES PATENT AND TRADEMARK OFFICE
CERTIFICATE OF CORRECTION

PATENT NO. : 4,728,509

DATED : March 1, 1988

INVENTOR(S) : Hisayoshi SHIMIZU et al.

It is certified that error appears in the above-identified patent and that said Letters Patent is hereby corrected as shown below:

(a) Column 10, claim 10, line 3; "10-10% (w/v)" should be "1-10% (w/v)".

Signed and Sealed this

Seventh Day of February, 1989

*Attest:*

DONALD J. QUIGG

*Attesting Officer*   *Commissioner of Patents and Trademarks*